United States Patent [19]
Shiery

[11] Patent Number: 5,732,741
[45] Date of Patent: Mar. 31, 1998

[54] NOISE SUPPRESSOR

[75] Inventor: Jeffrey C. Shiery, Parma, Mich.

[73] Assignee: Aeroquip Corporation, Maumee, Ohio

[21] Appl. No.: 719,895

[22] Filed: Sep. 25, 1996

[51] Int. Cl.[6] ........................... F16L 55/04
[52] U.S. Cl. ................... 138/30; 138/26; 220/720
[58] Field of Search .................. 138/30, 26, 31; 220/720, 721, 723

[56] References Cited

U.S. PATENT DOCUMENTS

| | | | |
|---|---|---|---|
| 2,760,518 | 8/1956 | Peet | 138/30 |
| 2,841,181 | 7/1958 | Hewitt et al. | 138/30 |
| 3,063,470 | 11/1962 | Forester | 138/30 |
| 3,380,480 | 4/1968 | Bleasdale | 138/30 |
| 3,741,250 | 6/1973 | Mercier | 138/30 |
| 3,744,527 | 7/1973 | Mercier | 138/30 |
| 3,948,287 | 4/1976 | Suginura et al. | 138/30 |
| 4,628,964 | 12/1986 | Suginura et al. | 138/30 |
| 4,732,176 | 3/1988 | Sugimura | 138/30 |
| 4,759,387 | 7/1988 | Arendt | 138/30 |

OTHER PUBLICATIONS

The Inline Suppressor for Hydraulic Noise & Shock brochure by Wiles & McLean Ltd., pp. 1-5.
Basic Sound Stuff Factory Noise brochure by Vickers, pp. 1-21.
Noise Control in Hydraulic Systems brochure by Vickers, 1992, pp. 1-13.
The Measured Transmission Loss Characteristics of Some Hydraulic Attenuators by R.J. Whitson, BSc, pp. 105-114.
Modelling of Flow Ripple from Fluid Power Piston Pumps by J-O. Palmberg, pp. 207-227.
Survey of the State of the Art and Computer Simulation on Reduction of Flow/Pressure Ripple in a Hydraulic System by Dong Zhun Sin, Professor Fronczak, May 15, 1992, 2 pages.
Hydrostatic Transmission Noise Abatement by G.E. Maroney & D.L. O'Neal for the Society of Automotive Engineers, Apr. 18-20, 1977, pp. 1-9.
Some Aspects of Hydraulic Noise Control Technology by Russ Henke, SAE Technical Paper Series, Sep. 10-13, 1984, 12 pages.
"Quiet Please!" Noise Control by Design brochure by Sperry Vickers, 1979, pp. 1-23.
The Measurement of the Fluid Borne Pressure Ripple Characteristics of Hydraulic Components by K.A. Edge, BSc, PhD, CEng. & T.J. Wing, BSc, PhD, Proc Instn Mech Engrs vol. 197B, pp. 247-254, Nov. 1983.

Primary Examiner—Patrick F. Brinson
Attorney, Agent, or Firm—Emch, Schaffer, Schaub & Porcello, Co., L.P.A.

[57] ABSTRACT

A noise suppressor device for absorbing and dampening the noise of pulsating fluids is disclosed. The noise suppressor device has a housing which defines an axially extending bore. A resilient bladder is coaxially positioned in the bore. A spool assembly is coaxially positioned within the bladder. The spool assembly has a spool layer and a sleeve layer which coaxially surrounds the inner spool layer. The spool layer and the sleeve layer define a tortuous path for fluid to flow through from the axial bore to the bladder.

10 Claims, 2 Drawing Sheets

NOISE SUPPRESSOR

TECHNICAL FIELD

The present invention relates to a fluid impulse and noise suppressor or dampener. In particular, the present invention relates to a noise suppressor having a bladder, bladder support spool, and noise dampening sleeve.

The present invention is especially useful in suppressing noise and in dampening the pulses of fluid moving in various hydraulic systems. In preferred embodiments, the noise suppressor is positioned in the hydraulic system near a pump outlet.

BACKGROUND OF THE INVENTION

The pulses (or changes in fluid pressure) in a fluid flow cause wear on hydraulic systems. Fluid impulse dampeners or suppressors are used in various hydraulic systems to compress or dampen the pulses of fluid which are flowing and pulsing through the hydraulic system. One type of suppressor comprises a housing having a pressure chamber defined between a flexible bladder and an interior surface of the housing. A pressurized gas is supplied to the pressure chamber. The interior of the bladder defines a fluid receiving chamber. The bladder is coaxially positioned over a tubular support or spool in the chamber. The support has radially extending perforations or holes. The fluid chamber receives the flow of fluid moving through the hydraulic system. The compressibility of the pulsed fluid is achieved as the fluid passes through the fluid chamber as follows: the peak of pulsing fluid passes out through the holes in the support and pushes against the bladder. The bladder expands into the pressure chamber. The pressurized gas on the opposite side of the bladder exerts a counter force on the bladder, thus minimizing or dampening the peak of the fluid pulse. The gas pressure pushes or acts against the bladder causing the bladder to be forced against the support spool. The pulsations of the fluid passing through the housing are absorbed or dampened in the fluid chamber due to the deflections (expansions and contractions) of the bladder and a consequent compression of the gas present in the pressure chamber.

The pulses of fluid also generate noise as the fluid flows through the hydraulic system. While the bladder expands and contracts to absorb the pulses of fluid, the sound waves being generated by the pulsing fluid still tend to reverberate through the fluid dampener or suppressor. The noise generated by the changes in the sound waves is often unacceptably high and causes undesirable banging or knocking noises in the hydraulic system.

The suppressor housings must also be adequately sealed to withstand the normal gas charge pressures, which are typically in the range of approximately 2000–3000 psi. The pulsations of the fluid cause the bladder to expand and contract and the bladder moves in the housing. In the past, it has been difficult to adequately seal the bladder in the housing of the suppressor so that fluid does not leak from the edges of the bladder into the gas pressure chamber and/or from the suppressor housing.

In addition, in currently used bladder-type suppressors, the normal gas charge pressures and the high temperatures of the fluids passing through the suppressors cause damage to the bladder. The bladder is under constant expansion and contraction pressures. Portions of the bladder come into repeated contact with the support stool. The bladder wears out at the areas on the bladder where the bladder contacts the spool. Portions of the bladder are removed from these contact areas due to the highly repetitive nature of the pulsing cycle of the fluid flowing through the suppressor. In particular, the portions of the bladder adjacent the holes in the spool are prematurely worn or torn-away. That is, the edges of the holes in the spool wear away at the bladder causing the bladder to prematurely wear out and fail.

Previous attempts to prevent damage to the bladder have included U.S. Pat. No. 4,759,387 which placed a helical wave band between a spool and a diaphragm. However, the diaphragm was still subject to undue wear. Other attempts include U.S. Pat. No. 4,628,964 which used a supporting cylinder comprised of a plurality of wire nets over a reinforcing cylinder. However, these previous attempts do not have sufficient durability needed in many types of hydraulic systems and the helical bands and wire nets tend to deform over time due to repeated exposure to pulsing fluids, thereby decreasing the effectiveness of the suppressors.

Therefore, there is a need for a suppressor which overcomes the above-described drawbacks and which has increased durability and which adequately dampens the noise level of the hydraulic system.

DISCLOSURE OF THE INVENTION

The present invention is directed to an improved noise suppressor. The present invention reduces wear on hydraulic systems, reduces the noise level of hydraulic systems, and is easily installed in existing hydraulic systems.

The noise suppressor has a longitudinally oriented housing which defines an axially extending bore. A bladder is coaxially positioned in the bore. The bladder is supported within the bore by a spool assembly. In preferred embodiments, the bladder is made of an elastic material such as a durable EPR or rubber-type material which results in extremely long service life and requires minimal servicing.

The spool assembly is coaxially positioned within the bladder. The spool assembly preferably includes a spool type device which defines a longitudinally extending bore. The bore in the spool assembly receives the fluid flowing through the hydraulic system. When pulses or changes in fluid pressure occur, the spool assembly provides a means for the fluid to flow into the bladder cavity.

The spool assembly of the present invention comprises a spool layer and a sleeve layer which is coaxially positioned over the spool layer. In a preferred embodiment, the spool and sleeve layers are comprised of suitably strong materials such as corrosion resistant materials. In especially preferred embodiments, the spool layer comprises an aluminum alloy while the sleeve layer comprises a plastic type material which has high mechanical strength and rigidity, high fatigue endurance, high resistance to repeated impact, excellent dimensional stability, wide end use temperature range, and good resistance to hydraulic fluids. In preferred embodiments, the sleeve layer can comprise thermoplastic materials, including, for example, acetyl resins such as crystalline thermoplastic homopolymers made by the polymerization of formaldehyde and sold under the trade name Delrin® by the DuPont de Neumers Company.

The spool layer defines a plurality of openings or perforations which extend radially from an inner surface to an outer surface of the inner spool layer. The perforations in the spool layer provide sufficient openings for the pulsating fluid to flow into the bladder.

The sleeve layer defines a cylinder that substantially surrounds the spool layer. In a preferred embodiment, the sleeve layer comprises a material having a preferred thickness which is less than the thickness of the spool layer.

The present invention is specifically directed to an improved spool assembly having two coaxial layers, a spool layer and a sleeve layer. In operation, a radially narrow circumferential gap is formed in the sleeve layer to allow fluid to flow from the spool layer to the bladder. The spool layer and the sleeve layer of the spool assembly are of a design which reduces wear on the bladder and reduces the noise level in the hydraulic system.

The outer diameter of the spool layer is substantially the same as the inner diameter of the sleeve layer. The inventor believes that the configuration of the spool layer and the path of travel of the pulsing fluid through the perforations in the spool layer tends to transmit the forces generated by the pulsing fluid to the spool layer and to the sleeve layer, rather than mainly to the flexible bladder. The noise suppressor of the present invention thus takes advantage of the entire structure of the noise suppressor, including the spool assembly as well as the bladder, to dampen the forces of the pulsing fluid and the noise waves generated by the pulsing fluid.

An additional advantage is that it is now possible to provide a noise suppressor device which can have interchangeable spool and/or sleeve layers which allows the noise suppressor device to be customized for the end user and yet allows the manufacturer of the noise suppressor device to maintain a reduced inventory of a specific noise suppressor devices. Further, it is now possible to provide the end use customer with a more specific noise suppressor device especially a tailored to meet the requirements of the end user.

Therefore, one object of the present invention is to provide a noise suppressor device having improved noise dampening characteristics.

It is further object of the invention to provide an improved noise suppression device having a spool assembly which provides an increased useful life to the resilient bladder in the noise suppressor.

BEST MODE OF CARRYING OUT INVENTION

Figure 1:
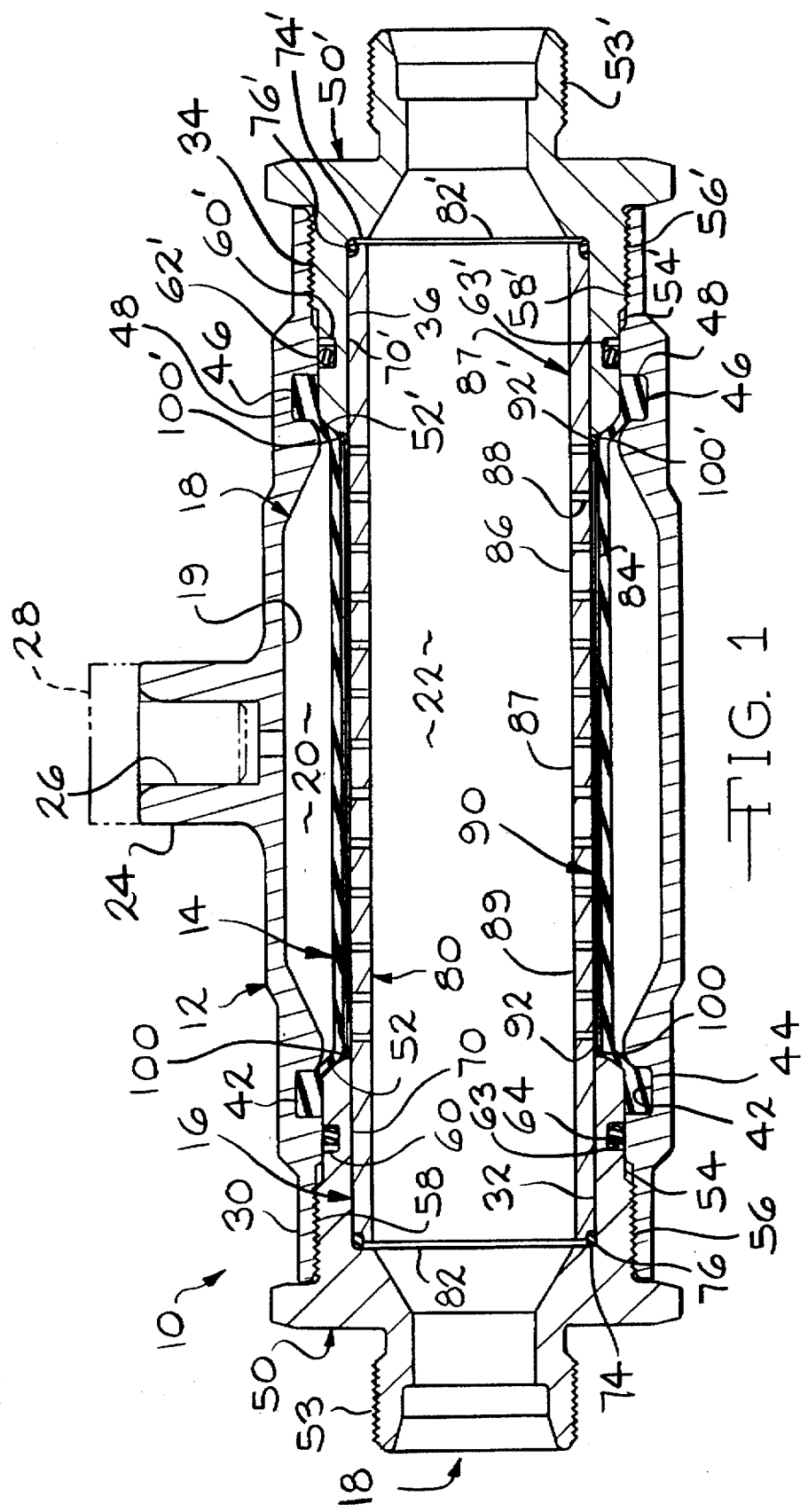
FIG. 1 is a sectional view of a noise suppressor device of the present invention.
Figure 2:
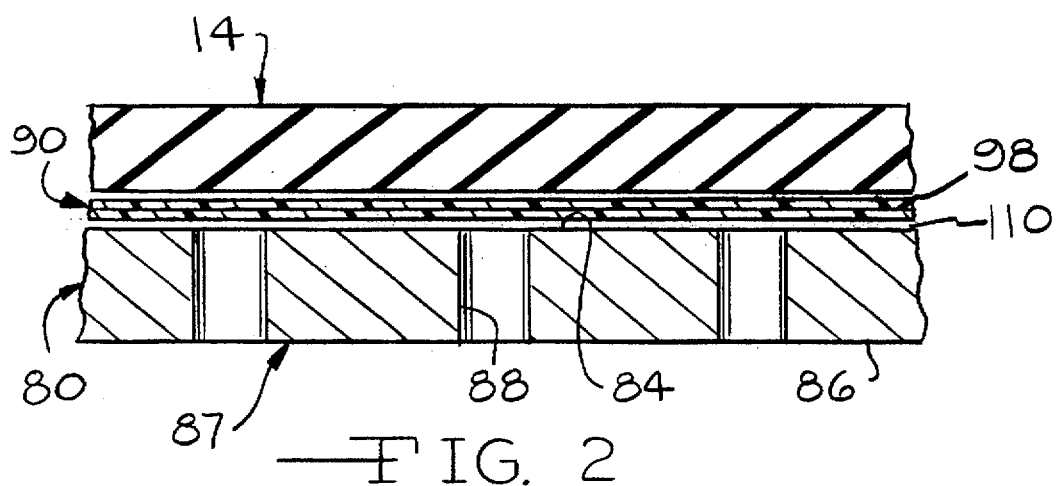
FIG. 2 is a sectional view showing an enlarged segment of the noise suppressor device of FIG. 1, having no pressure or an equilibrium of pressure of fluid against one side of the bladder and pressure of gas on an opposing side of the bladder.

FIG. 1 generally shows a noise suppressor device 10 comprising a housing 12, a generally hollow flexible bladder 14, and a spool assembly 16. The bladder 14 is coaxially positioned within a longitudinally extending bore 18 in the housing 12. The spool assembly 16 is coaxially positioned within the bladder 14. The shape of the longitudinally extending bore 18 through the housing 12 is defined by an inner surface 19 of the housing 12. The inner surface 19 and the bladder 14 define a pressure chamber 20 while the hollow bladder 14 and the spool assembly 16 define a fluid chamber 22.

The housing 12 further comprises a charging port 24 which defines a radially extending bore 26 for receiving a high pressure charging valve 28, shown in phantom. The radially extending bore 26 is in communication with the pressure chamber 20. A supply of a gas, such as nitrogen, is introduced under pressure to the pressure chamber 20.

The longitudinally extending bore 18 of the housing 12 has a first end 30 having a first interior surface 32 and a second end 34 having a second interior surface 36. The interior surfaces 32 and 36 engagingly receive the spool assembly 16. The housing 12 further defines a first groove or detent 42 for receiving a first end 44 of the bladder 14 and a second groove or detent 46 for receiving a second end 48 of the bladder 14.

The noise suppressor device 10 further includes a first adapter 50 axially positioned within the first end 30 of the housing 12 and a second adapter 50' axially positioned within the second end 34 of the housing 12.

In the embodiment shown, the first adapter 50 comprises a first end 52 which is positioned adjacent the bladder 14 when the adapter 50 is in position in the housing 12 and a second, opposing end 53 which is external to the housing 12 for receiving a hose or other coupling means, not shown. The first adapter 50 has an exterior surface 54 which includes a threaded portion 56 located between the first end 52 and the second end 53. The threaded portion 56 engages a corresponding threaded portion 58 on the interior surface 32 of the first opening 30. The first adapter 50 further includes a detent or groove 60 which circumferentially extends around the exterior surface 54. The detent or groove 60 receives a packing or sealing member 62, such as an O-ring and washer 63, for sealing the first adapter 50 into the opening 30 of the housing 12.

The first end 52 of the adapter 50 can have an angled or sloped surface to readily engage the first end 44 of the bladder 14. The first end 52 and the exterior surface 54 of the first adapter 50 secure the first end 44 of the bladder 14 in the detent 42 of the housing 12.

The first adapter 50 has an interior surface 70 which defines a flange portion 74. The interior surface 70 of the first adapter 50 axially receives the spool assembly 16. In a preferred embodiment, the spool assembly 16 is held in position against the interior surface 70 of the first adapter 50. In certain embodiments, a packing or sealing member 76 is positioned adjacent the interior flange portion 74 to secure the spool assembly 16 within the first adapter 50.

The noise suppressor device 10 further includes the second adapter 50' which is axially positioned within the second end 34 of the housing 12. In the embodiment shown, the first adapter 50 and the second adapter 50' have substantially the same shape or configuration; however, it is to be understood that it is within the contemplated scope of the present invention that the first adapter 50 and the second adapter 50' can have differently shaped configurations to allow for the installation of different couplings or hoses on the distal ends 53 and 53' of the first adapter 50 and second adapter 50', respectively.

In the embodiment shown, the second adapter 50' comprises a first end 52' which is positioned adjacent the bladder 14 when the second adapter 50' is in position in the housing 12 and a second, opposing end 53' which is external to the housing 12 for receiving a hose or other coupling means, not shown. The second adapter 50' has an exterior surface 54' which includes a threaded portion 56' located between the first end 52' and the second end 53'. The threaded portion 56' engages a corresponding threaded portion 58' on the interior surface 36 of the second opening 34. The second adapter 50' further includes a detent or groove 60' which circumferentially extends around the exterior surface 54'. The detent or groove 60' receives a packing or sealing member 62', such as an O-ring and washer 63', for sealing the second adapter 50' into the second opening 34 of the housing 12.

The first end 52' of the second adapter 50' can have an angled or sloped surface to readily engage the second end 48 of the bladder 14. The first end 52' and the exterior surface 54' of the second end 50' secure the second end 48 of the bladder 14 in the second detent 46 of the housing 12.

The second adapter 50' has an interior surface 70' which defines a flange portion 74'. The interior surface 70' of the second adapter 50' also axially receives the spool assembly 16. In a preferred embodiment, the spool assembly 16 is held in position against the interior surface 70' of the second adapter 50'. In certain embodiments, a packing or sealing member 76' is positioned adjacent the interior flange 74' to secure the spool assembly 16 within the second adapter 50'.

The spool assembly 16 comprises a spool layer 80 and a sleeve layer 90. The spool layer 80 is coaxially positioned within the bladder 14. The spool layer 80 has a first end 82 which is adjacent the first adapter 50 and a second end 82' which is adjacent the second adapter 50'. The first end 82 and second end 82' are held in position against the sealing members 74 and 74', respectively. The spool layer 80 has an outer surface 84 and an inner surface 86.

A plurality of radially extending perforations 88 extend through the spool layer 80 from the outer surface 84 to the inner surface 86. The perforations 88 are preferably evenly spaced along at least a center portion 89 of the spool layer 80. The perforations 88 are arranged in a pattern on the spool layer 80. In a preferred embodiment, the perforations 88 in the center portion 89 begin at a point adjacent the first end 52 of the first adapter 50 and terminate at a point adjacent the second end 52' and the second adapter 50'. The generally evenly spaced perforations 88 on the spool layer 80 provides sufficient openings for changes in fluid pressure to pass through the perforations 88.

The inner surface 86 of the spool layer 80 defines an axially extending bore 87. The axially extending bore 87 is sealed from the interior chamber 20 by the first end 44 and second end 48 of the bladder 14.

The sleeve layer 90 comprises a first end 92 which is adjacent the first adapter 50 and a second end 92' which is adjacent the second adapter 50'. The sleeve layer 90 is coaxially positioned on the spool layer 80 and is positioned between the bladder 14 and the spool layer 80.

Figure 4:
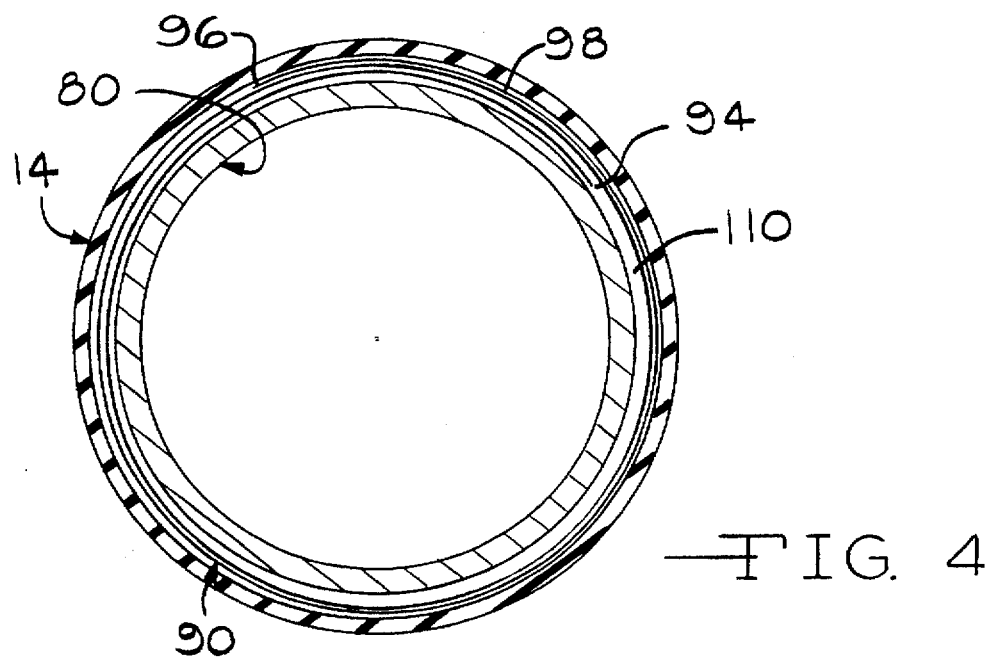
FIG. 4 is a cross-sectional view of the noise suppressor device of FIG. 1 showing the spool assembly and the bladder.

In certain preferred embodiments, the sleeve layer 90 comprises an open or expandable cylindrical or curved material having the first end 92, a second opposing end 92', a longitudinally oriented leading or inner edge 94 and an opposing longitudinally oriented trailing or outer edge 96, as best seen in FIG. 4. In preferred embodiments, the sleeve layer 90 completely wraps around the spool layer 80 such that two layers of the sleeve material wrap the spool layer 80 and the leading edge 94 is usually not aligned with the trailing edge 96. That is, the leading edge 94 longitudinally extends from the first end 92 of the sleeve layer 90 to the second end 92' and is positioned adjacent the spool layer 80. A curved central portion 98 which is defined between the leading edge 94 and the trailing edge 96, of the sleeve layer 90 substantially surrounds the spool layer 80 and is preferably comprised of two layers of sleeve material, thereby forming a circumferential gap between the layers. The trailing edge 96 also longitudinally extends from the first end 92 of the sleeve layer 90 to the second end 92'. The trailing edge 96 is positioned adjacent the bladder 14, separated from the spool layer 80 by the central portion 98 of the sleeve layer 90, and is preferably not aligned with the leading edge 94. While the preferred embodiment envisions two layers of sleeve material wrapping the spool layer 80, the actual amount of sleeve material utilized to wrap the spool layer 80 may be varied, depending upon design considerations.

In certain embodiments, the spool assembly 16 further comprises a first spacer 100 which is coaxially positioned adjacent the first end 92 of the sleeve layer 90 and a second spacer 100' coaxially positioned adjacent the second end 92' of the sleeve layer 90. It is to be understood however, that the present invention is also useful with one spacer positioned adjacent at least one of the ends of the outer spool layer.

In a preferred embodiment, the spool layer 80 defines a first thickness or width between the outer surface 84 and the inner surface 86 and the sleeve layer 90 defines a second thickness or width. In a preferred embodiment, the thickness or width of the spool layer 80 is greater than the thickness or width of the sleeve layer 90.

In certain preferred embodiments, the sleeve layer 90 has a single-layer thickness ranging from about 0.01 to about 0.03 inches and most preferably about 0.01 inches while the spool layer 80 is approximately 2–4 times thicker than the sleeve layer 90 single layer thickness. The sleeve layer 90 preferably is coaxially positioned over and engages the spool layer 80 such that there is no clearance between the sleeve layer 90 and the spool layer 80. In a preferred embodiment, the sleeve layer 90 has an inside diameter which is approximately 5% to about 15%, and more preferably about 10% smaller than the outside diameter of the spool layer 80, such that the sleeve layer 90 must be stretched to engage the spool layer 80, thereby creating a tight fit between the sleeve layer 90 and the spool layer 80.

In operation, it is envisioned that the sleeve layer 90 will provide a tortuous path for the fluid to flow from the axial bore 87 through the perforations 88, past the leading edge 94, through the gap and center portion 98 between the over-lapped layers of the sleeve layer 90, past the trailing edge 96, and finally contacting the bladder 14. Alternatively, it is envisioned that the sleeve layer will expand with the bladder surface and partially unwrap as the bladder compresses, with little or no fluid flow between the over-lapped layers. However, in either mode of operation, any fluid flowing through the noise suppressor device 10 will be exposed to the flow paths between the sleeve layer 90 and spool layer 80.

Figure 3:
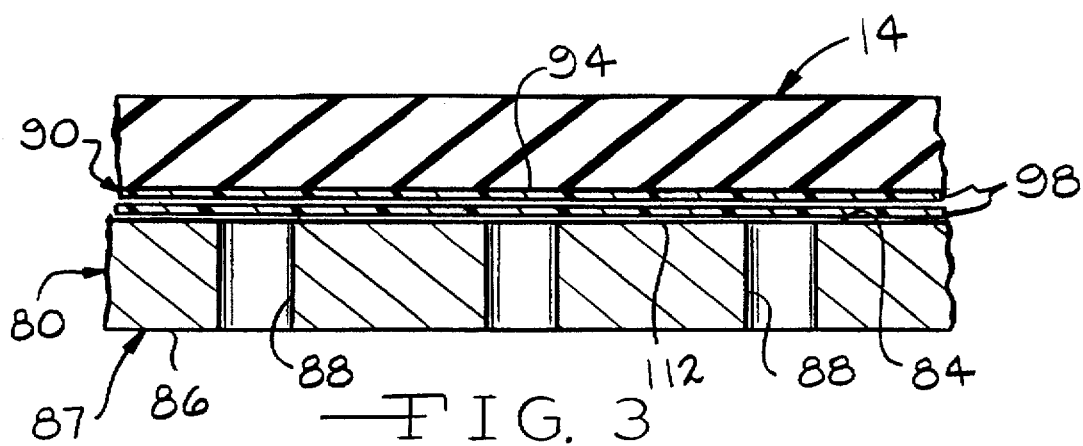
FIG. 3 is a sectional view, similar to FIG. 2, but showing lesser pressure of fluid against a bladder than pressure of gas on an opposing side of the bladder.

The fluid flows through the axial bore 87 in the spool layer 80 and through the perforations 88 in the spool layer 80. As fluid pressure increases, the fluid is forced into the gap between the overlapping sections of the sleeve layer 90. The fluid forces the trailing edge 96 against the bladder 14 causing the bladder 14 to expand and absorb the fluid impulse and the sound waves, as shown in FIG. 3. The fluid also contacts the bladder 14 causing the bladder 14 to expand or distend into the pressure chamber 20. The gas pressure on the bladder 14 keeps the bladder 14 from expanding too far during peak or pulse periods of fluid passing through the axial bore 87. The gas in the pressure chamber 20 is compressed, thus dampening or absorbing the forces and sound waves of the pulsing fluid.

In a preferred embodiment, a suitable sleeve layer 90 comprises a thermoplastic sheet that is cut to the desired dimensions. The thermoplastic sheet is rolled into a cylindrical shape and is removably inserted into the interior of a tube (not shown). The tube and cylindrical shaped thermoplastic sheet are heated to a desired temperature such that the thermoplastic sheet substantially conforms to the inside diameter of the tube. The thermoplastic sheet retains its cylindrical shape upon cooling, thus forming the sleeve layer 90. It is to be understood, however, that other suitable means for forming the sleeve layer are also within the contemplated scope of the present invention.

While the invention has been described in terms of various preferred embodiments, the skilled artisan will appreciate the various modifications and substitutions, omissions and changes which may be made without departing from the spirit thereof. Accordingly, it is intended that the scope of the present invention be defined solely by the scope of the following claims including the equivalents thereof.

I claim:

1. A noise suppressor device comprising:

a housing defining an axially extending bore through which pressurized fluid flows;

a bladder coaxially positioned in the bore; and a spool assembly coaxially positioned within the bladder, the spool assembly including a spool layer with radially oriented perforations extending therethrough and a sleeve layer which axially wraps the outside surface of the spool layer, the sleeve layer being substantially thinner than the spool layer and circumferentially overlapping itself as it circumferentially wraps the spool layer;

the sleeve layer including an axially extending leading edge and an axially trailing edge, wherein a radially expandable circumferential gap is defined between the circumferentially overlapped layers of the sleeve, the gap extending from the leading edge of the sleeve layer to the trailing edge when the sleeve layer is subjected to pressure from the pressurized fluid, the gap defining a spiral path for the pressurized fluid between the circumferentially overlapped layers of the sleeve layer of the spool assembly and the bladder.

2. The noise suppressor device of claim 1, wherein the spool layer includes a specified outside diameter and sleeve layer includes a specified inside diameter, the outside diameter being substantially equivalent to the inside diameter.

3. The noise suppressor device of claim 1, wherein the spool includes a specified outside diameter and the sleeve layer includes an inside diameter smaller than the outside diameter, such that the sleeve layer is radially stretched to wrap the spool layer.

4. The noise suppressor device of claim 1, wherein the spool layer comprises an aluminum alloy and the sleeve layer comprises a thermoplastic material.

5. The noise suppressor device of claim 1, wherein the housing has a first end for receiving a first adapter and a second end for receiving a second adapter, the first and second adapters securing the bladder within the housing.

6. The noise suppressor device of claim 5, wherein the spool layer has a first end secured by the first adapter and a second end secured by the second adapter.

7. The noise suppressor device of claim 1, wherein the bladder and housing define a pressure chamber which is pressurized to counteract the forces exerted on the bladder by the pressurized fluid flow.

8. The noise suppressor device of claim 1, wherein at least two layers of the sleeve layer circumferentially extend around the spool layer, and wherein the leading edge of the sleeve layer is not aligned with the trailing edge of the spool layer.

9. The noise suppressor device of claim 1 wherein the sleeve layer engages the spool layer such that there is substantially no clearance between the sleeve layer and the spool layer when there is no pressurized fluid flowing through the noise suppressor device.

10. The noise suppressor device of claim 9, wherein the sleeve layer has an inside diameter which is approximately 5 to about 15% smaller than an outside diameter of the spool layer.

* * * * *